(12) United States Patent
McCreery et al.

(10) Patent No.: US 6,304,785 B1
(45) Date of Patent: Oct. 16, 2001

(54) ELECTRODE INSERTION TOOL

(75) Inventors: Douglas B. McCreery, Pasadena; Leo A. Bullara, Glendora; Stephen H. Waldron, Camarillo, all of CA (US)

(73) Assignee: Huntington Medical Research Institute, Pasadena, CA (US)

( * ) Notice: Subject to any disclaimer, the term of this patent is extended or adjusted under 35 U.S.C. 154(b) by 0 days.

(21) Appl. No.: 09/428,672

(22) Filed: Oct. 27, 1999

Related U.S. Application Data
(60) Provisional application No. 60/105,896, filed on Oct. 27, 1998.

(51) Int. Cl.$^7$ .............................. A61N 1/05; A61B 19/00
(52) U.S. Cl. ...................... 607/116; 607/117; 607/137; 600/377; 128/899; 606/129
(58) Field of Search ............................ 600/377–379; 607/116, 117, 137; 128/899; 606/129, 167, 185; 604/130, 51, 134, 135

(56) References Cited

U.S. PATENT DOCUMENTS

| | | | |
|---|---|---|---|
| 5,306,251 | * 4/1994 | Alexander | 604/130 |
| 5,361,760 | 11/1994 | Normann et al. | 128/642 |
| 5,443,493 | * 8/1995 | Byers et al. | 607/137 |
| 6,056,716 | * 5/2000 | D'Antonio et al. | 604/68 |

OTHER PUBLICATIONS

Annals of Biomedical Engineering (1992) pp. 413–422.

A Microassembly Structure for Intracortical Three–Dimensional Electrode Arrays (1996) five pages.

* cited by examiner

*Primary Examiner*—Kennedy Schaetzle
(74) *Attorney, Agent, or Firm*—Christie, Parker & Hale, LLP

(57) ABSTRACT

A tool for inserting medical electrodes such as nerve-stimulating electrodes into tissue. An electrode is positioned fully within a tip of the tool so the tip end can be placed directly against the tissue to be penetrated for precise handheld positioning. A trigger on the tool is actuated to release a compressed spring in the tool to drive the electrode out of the tool tip into the target tissue. A viscous-damping means is provided in the tool to control electrode acceleration and velocity.

6 Claims, 5 Drawing Sheets

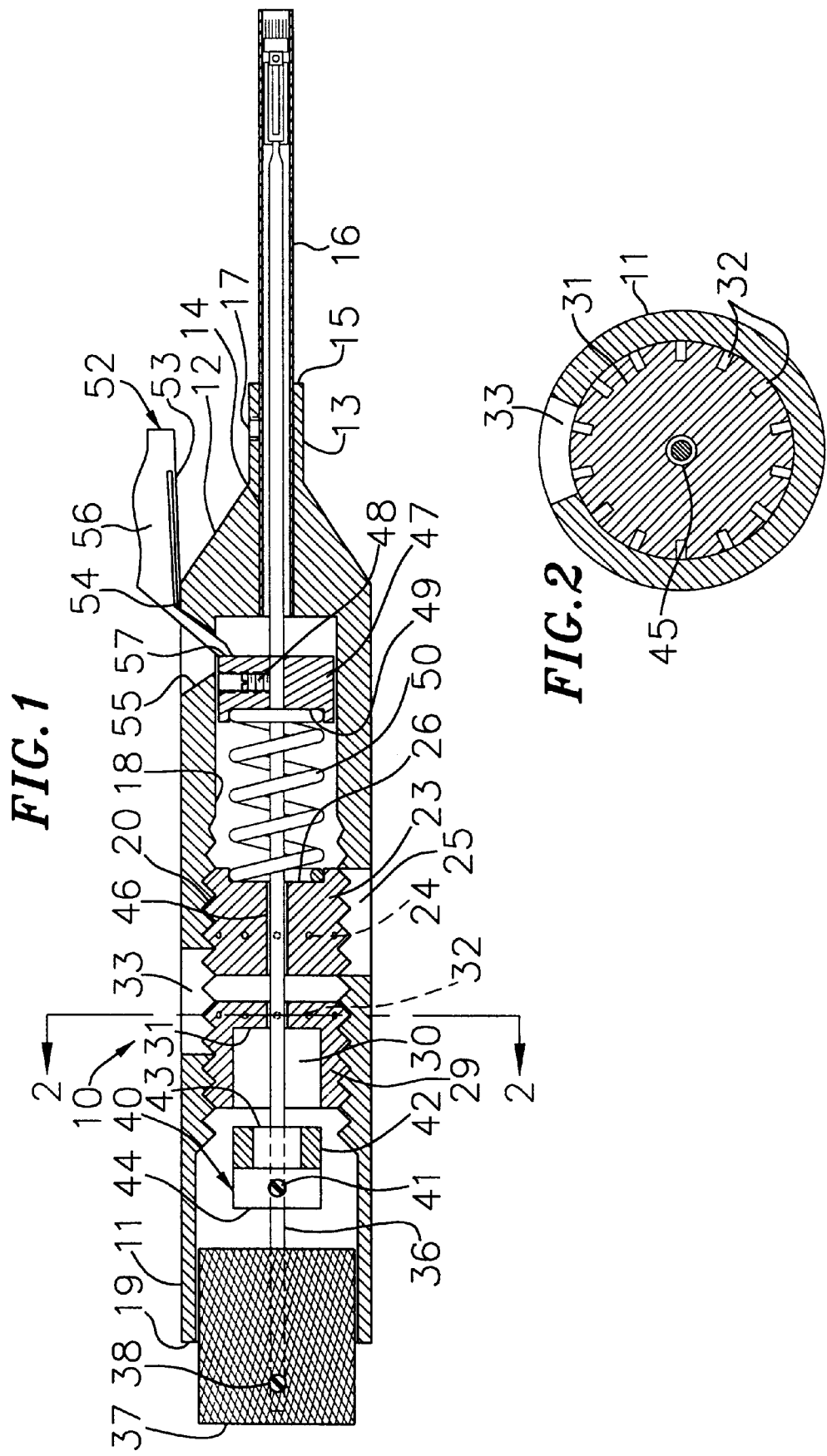

ELECTRODE INSERTION TOOL

CROSS-REFERENCE TO RELATED APPLICATION

This application claims the benefit of U.S. Provisional Application 60/105,896 filed Oct. 27, 1998.

STATEMENT REGARDING FEDERALLY SPONSORED RESEARCH OR DEVELOPMENT

The development of the invention disclosed in this application was in part funded under NIH Contracts N01-DC-5-2105 and N01-DC-8-2102

BACKGROUND OF THE INVENTION

This invention relates to a simple and reliable mechanical tool for inserting medical electrodes into nerve tissue such as the cerebral cortex, brain stem and the spinal cord. The tool can be hand held, or mounted in a stereotactic positioning device. An alternative embodiment of the tool uses a curved tip for holding the electrode for insertion in the cochlear nucleus of the brain as part of a procedure to assist a profoundly deaf patient.

The tool is especially useful with small medical electrodes having a button-like cylindrical base, typically made of epoxy, of about 2.5-mm diameter and about 0.5-mm thickness. Typically, multiple (e.g., seven) relatively sharp time-like electrodes (the length depending on the application, but typically in the range of 1 to 6 mm) extend from the base, and connecting leads enable individual or parallel energization of the electrodes depending on the nerve-stimulation protocol being used.

The challenge met by the invention is to move the positioned electrode with an initially high acceleration to enable the electrode times to penetrate at high velocity the tough and puncture-resistant pia-arachnoid member overlapping the cortex and spinal cord. It is then desirable to stabilize and cease accelerating the penetration rate to prevent injury to the underlying neuron al population, and to the delicate arterial and venous blood vessels.

An important advantage of the invention is that the electrodes and associated base are recessed within a tip of the insertion tool prior to actuation. This feature enables the tool tip to be positioned against the tissue to be penetrated, thus enabling handheld operation as opposed to the sometimes cumbersome mounting of the tool in a stereotactic positioning device.

Several alternative velocity-control mechanisms are disclosed which approximate viscous damping of movement of the electrode driving mechanism to enable high initial acceleration until penetration is achieved, with controlled and relatively stabilized velocity thereafter.

SUMMARY OF THE INVENTION

The electrode insertion tool of this invention includes a tubular handle having a reduced-diameter tubular tip. A guide wire extends through the handle and into the tip to be secured to an injection piston slidably moveable within the tip. An electrode assembly can be fully inserted against the injection piston to be shrouded by the tip, thus enabling the tip to be placed directly against the tissue into which the electrode assembly is to be inserted.

A compression spring is positioned within the handle, and is compressed between an adjustable normally stationary plug and a moveable ring which is secured to the guide wire. A cocking knob extends from a rear end of the handle and is secured to the guide wire so the knob can be retracted to move the ring toward the stationary plug to compress the spring. An external trigger on the handle holds the plug in the spring-compressed "cocked" position, and the trigger is moveable to release the plug and "fire" the tool to move the electrode assembly forwardly out of the tubular tip.

To provide a high initial acceleration of the guide wire and electrode assembly, followed by a relatively constant velocity (typically in the range of one-to-four meters per second), a means is provided within the handle to provide motion control approximating viscous damping, and restraining force approximately proportional to velocity of the moving system, thus enabling high initial acceleration. The damping means is described in terms of both magnetic eddy-current braking force, and piston-cylinder drag force.

DESCRIPTION OF THE DRAWINGS

FIG. 1 is a side elevational view, partly broken away and in cross section, of the tool of this invention;

FIG. 2 is a sectional end view on line 2—2 of FIG. 1;

DESCRIPTION OF THE PREFERRED EMBODIMENT

Figure 3:
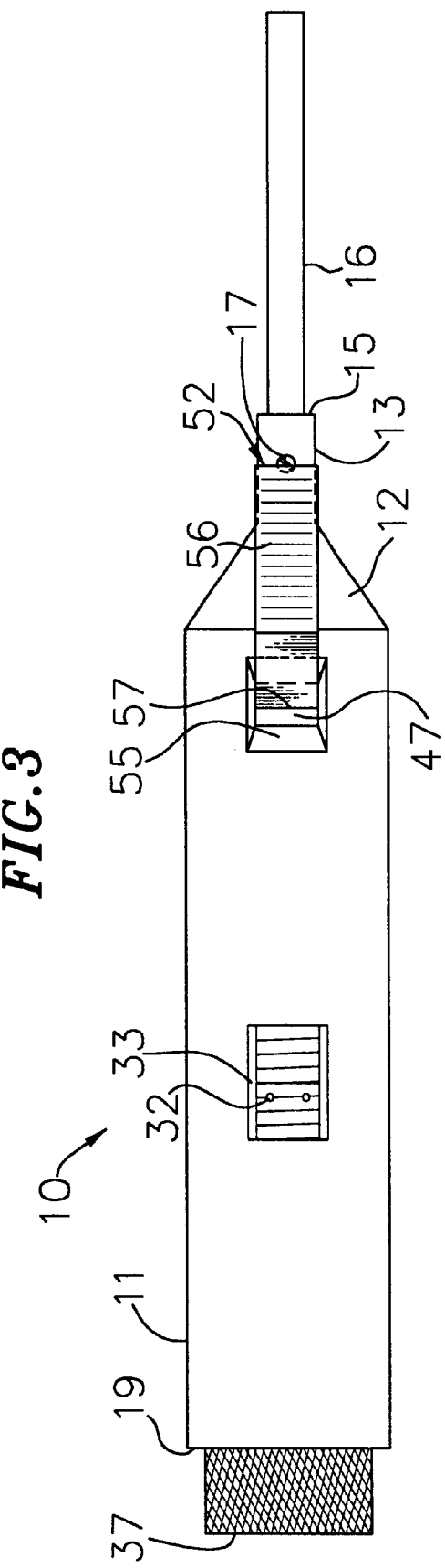
FIG. 3 is a top view of the tool shown in FIG. 1.

Referring to FIGS. 1 and 2, an electrode insertion tool 10 according to the invention has a hollow cylindrical handle 11 extending to an inwardly tapered portion 12 and a tubular extension 13. A bore 14 extends centrally through portion 12 and extension 13 at a forward end 15 of the handle at the right side of FIG. 1. A hollow tube 16 is rigidly secured by a set screw 17 or other fastening means to the handle within bore 14, and extends from forward end 15 of the handle.

A larger diameter bore 18 extends from the inner end of tube 16 to a rear end 19 of the handle, and a central part of the bore defines internal threads 20. An externally threaded spring-compression plug 23 is fitted within the handle in engagement with threads 20 to be axially adjustable in position. Extending around the circumference of the plug are depressions 24 which are accessible through a slot 25 in the handle, and through which a pin (not shown) can be inserted to turn the plug for axial position adjustment. A spring-seat recess 26 is formed in a forward end of the plug.

An externally threaded cup-shaped copper ring 29 is positioned rearwardly of plug 23 within the handle in engagement with threads 20 to be axially adjustable in position. Ring 29 has a central recess 30, and a closed end 31, and in common with plug 23, has circumferentially extending depressions 32 accessible through a slot 33 in the handle sidewall (FIG. 2) to enable the ring to be rotated to a desired axial position.

A drive rod 36 extends centrally through the handle and tube 15, and is anchored at its rear end in an externally knurled cylindrical cocking knob 37 by a set screw 38. A forward end of knob 37 makes a slip fit within bore 18 of the handle, and an opposite end of the knob extends rearwardly beyond the rear end of the handle so it can be grasped and moved rearwardly to cock the tool as described below.

A velocity damper 40 is rigidly secured by a set screw 41 to drive rod 36 forwardly of cocking knob 37 and spaced rearwardly from the open end of copper ring 29 when the tool is in a cocked position as shown in FIG. 1. A ring magnet 42, preferably made of samarium, is at the front end of damper 40 in a position to make a slip fit within recess 30 of the copper ring, and is glued or otherwise secured to a central stub 43 of an aluminum locking ring 44 which is secured to the drive rod by setscrew 41.

Drive rod 36 continues forwardly through a central clearance opening 45 (FIG. 2) in closed end 31 of copper ring 29, and through a similar central clearance opening 46 in spring compression plug 23 to extend through and to be rigidly and centrally secured to a forward spring seat ring 47 by a setscrew 48. The rear end of ring 47 defines a recess 49, and a compression coil spring 50 is seated at its forward end in recess 49, and at its rear end in recess 26 of plug 23.

A trigger 52 has a slender and resilient lower band 53 which is welded at 54 to the outer surface of handle 11 just forward of a slot 55 through the handle sidewall adjacent the forward surface of ring 47. A forward end of band 53 is integrally joined to a thicker and stiff upper knurled member 56, the rear end of which extends inwardly through slot 55 to a tip 57 which bears against the forward surface of ring 47 to restrain movement of the ring which the tool is cocked by withdrawing cocking knob 37 to compress spring 50. Depression of the forward end of upper member 56 bends lower band 53, and lifts tip 57 out of engagement with ring 47 to operate the insertion tool.

Figure 4:
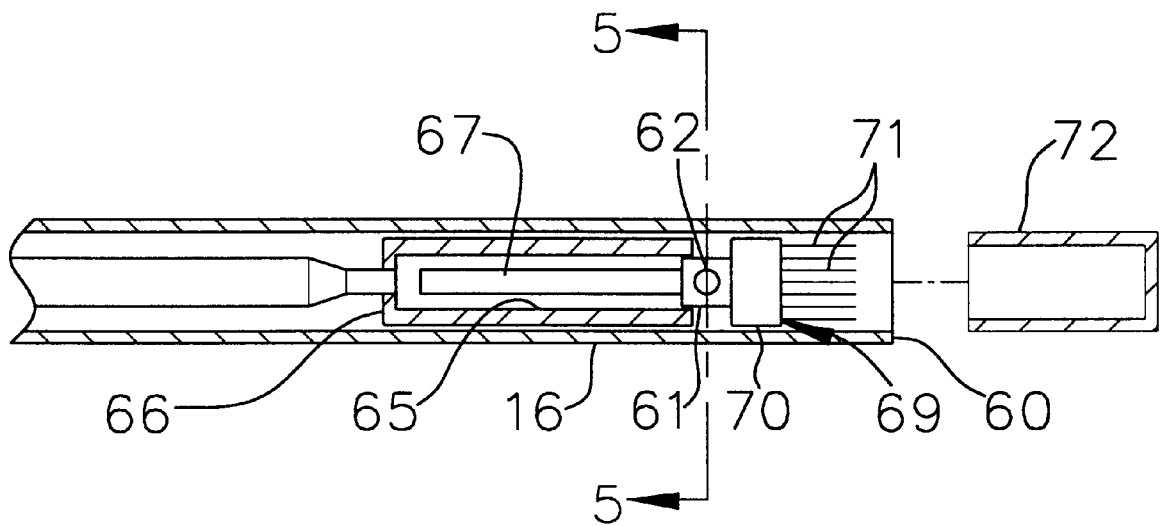
FIG. 4 is an enlarged sectional view of the tool tip at the right end of FIG. 1.
Figure 5:
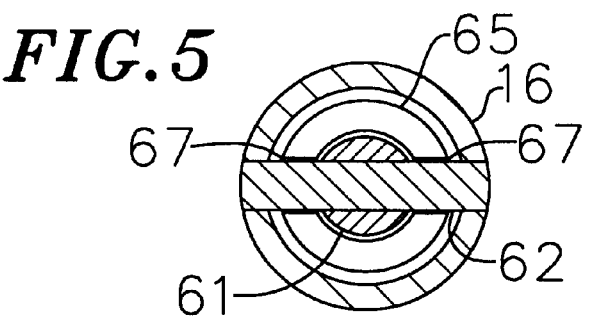
FIG. 5 is a sectional end view on line 5—5 of FIG. 4.

Referring to enlarged FIGS. 4 and 5, hollow tube 16 extends from handle 11 to a forward open end 60. A cylindrical electrode support post 61 is centrally positioned within tube 16 rearwardly of forward end 60, and is rigidly secured to the tube by a pin 62 which is anchored in opposed sidewalls of the tube, and is secured to and extends through the post as shown in FIG. 5.

An injection cylinder 65 is positioned within tube 16, and has a closed end 66 which is rigidly secured to the forward end of drive rod 36. The cylinder has an internal bore which is larger in diameter than the outside diameter of support post 61, and is fitted slightly over and in axial alignment with the support post. A pair of slots 67 are formed in opposed sidewalls of the cylinder in alignment with pin 62 so the cylinder can be moved forwardly along the support post when the tool is activated.

An electrode assembly 69 having a short cylindrical base 70 and multiple time-like electrodes 71 is positioned within the forward end of tube 16, with the sharpened tips of the electrodes being positioned slightly rearwardly of the forward end of the tube. The electrode assembly is most easily so positioned by a cylindrical insertion tube 72 which makes a slip fit within tube 16 and around electrodes 71 to press against the forward end of base 70 ,and thus push the assembly against the support post.

Before insertion, a relatively weak medical-grade adhesive is applied to the forward end of the support post, or to the rear surface of base 70. This adhesive weakly secures the inserted electrode assembly to the support post, but the bond is easily broken when the tool is activated to drive the injection cylinder forwardly against the electrode assembly base. A suitable pressure-sensitive silicone-based adhesive is available from NuSil Technology in Carpenteria, Calif., as Product No. PSA 9839 (biocompatible).

With the electrode assembly thus positioned within the insertion tool, the end of tube 16 is positioned over the nerve-tissue area to be penetrated, and trigger 52 is depressed to release ring 47 from trigger tip 57, and thereby to activate or "fire" the tool. Initial acceleration of the drive rod, injection cylinder, and other attached components is rapid and unimpeded to insure quick penetration of the relatively tough PA-arachnoid membrane which overlies the target nerve tissue. Thereafter, magnet 42 moves forwardly within copper ring 29, and the resulting movement-generated eddy current impedes and slows the initial rapid movement of the electrode assembly to minimize the risk of injury to the target nerve tissue.

Typically, handle 11 is about 10 cm in length, and tube 16 extends about 4 cm beyond the forward end of the handle. Apart from the materials previously specified, the tool components are preferably made from stainless steel to withstand sterilization by autoclaving or similar processes.

Figure 6:
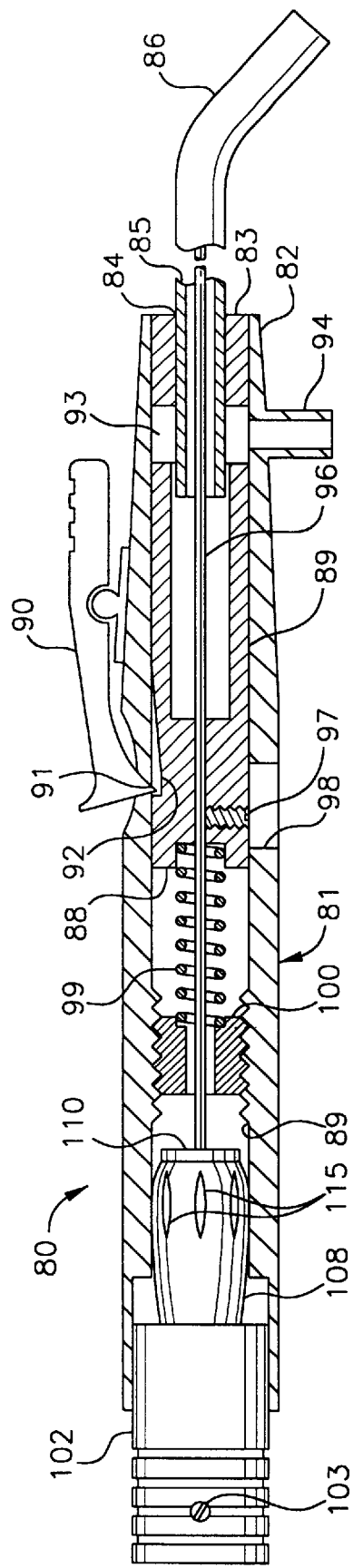
FIG. 6 is a sectional side elevation of a second embodiment of the tool.
Figure 8:
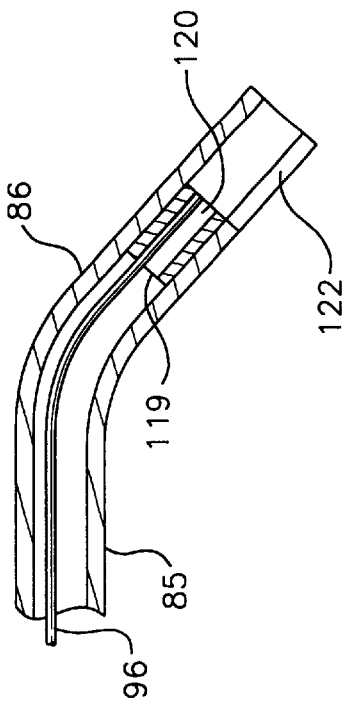
FIG. 8 is an enlarged sectional elevation of a curved tip used in the tool of FIGS. 6 and 7.
Figure 7:
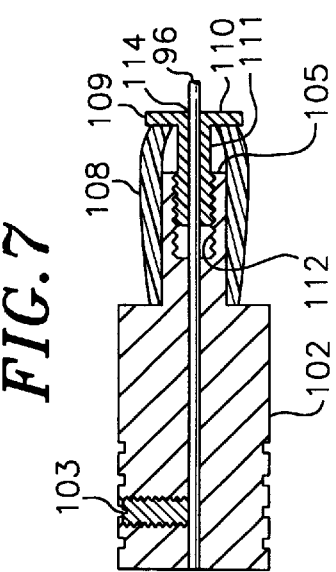
FIG. 7 is an enlarged view of a viscous damper used in the second embodiment.

FIGS. 6–8 show a second embodiment of an electrode insertion tool 80 which differs from tool 10 in several ways. First, an adjustable viscous friction damper is substituted for the magnetic damper of tool 10 to provide additional damping force to control electrode insertion speed. Second, a curved insertion tip is provided for improved access to the cochlear nucleus for insertion of an electrode used in an auditory-prosthesis system. Third, the electrode is held in the tip by a partial vacuum which is released when the electrode is inserted to enable immediate removal of the tool.

Tool 80 includes a hollow cylindrical housing 81 which is closed at a forward end 82 by a press-fitted plug 83 having a central opening 84 in which is rigidly secured the rear end of a hollow tube 85 having a curved tip 86 which extends at an angle of about 55 degrees from the central axis of tube 85. A cylindrical piston 88 makes a close slip fit within a central bore 89 in housing 81. A trigger 90 is pivotally mounted on the outer surface of the housing, and has a tip 91 which is spring urged downwardly into engagement with a recess 92 in piston 88 when the tool is cocked as shown in FIG. 6.

A chamber 93 is formed within the housing between the front end of the piston, and the rear surface of plug 83, and a laterally extending tube 94 secured to the housing opens into the chamber and is adapted for connection to a vacuum pump so the pressure in the chamber can be reduced below ambient atmospheric pressure. A drive wire 96 extends centrally completely through housing 81 and tube 85, and corresponds in function to drive rod 36 of tool 10. Piston 88 is secured to the drive wire by a set screw 97 which is accessible through a small slot 98 in the sidewall of the handle. The outer end of set screw 97 may be extended (not shown) to fit within slot 98 and bottom against the forward end of the slot to provide a positive movement stop.

A compression coil spring 99 is positioned within the housing between the rear end of piston 88 and the front surface of a longitudinally adjustable spring compression plug 100 corresponding to plug 23 in tool 10. The plug has a central clearance opening through which drive wire 96 extends.

A cylindrical cocking knob 102 (corresponding to knob 37 of tool 10) makes a slip fit within the rear end of housing 81, and is secured to the rear end of the drive wire by a setscrew 103. A reduced diameter sleeve 105 (FIG. 7) extends forwardly from the knob within central bore 89 of the housing between the knob and plug 100.

Fitted over the end of sleeve 105 forwardly of knob 102 is a silicone-rubber tube 108 having a rear end which abuts the end of the knob, and a front end which contacts an enlarged head 109 to a plastic screw 110 having a shank 111 threaded into a mating central bore 112 of sleeve 105. Screw 110 has a central opening 114 therethrough to provide clearance for drive wire 96. Preferably, a plurality of slits 115 are cut in the forward end of tube 108 enabling the tube to be longitudinally compressed by tightening screw 110, and thereby enlarging in diameter to contact the surface of bore 89 as shown in FIG. 6. The outer surface of tube 108 and the inner surface of bore 89 are coated with a viscous material (high-vacuum silicone grease as available from Dow Corning is suitable) to provide a viscous damping force opposing forward movement of the cocking knob and drive wire at a level proportional to the forward velocity of these moving parts. The force level is adjustable by rotating screw 110 to vary the compressive force exerted by the screw head against tube 108.

Referring to FIG. 8, fitted within the forward or outer end of curved tubular tip 86 of tube 85 is a hollow injection piston 119 which makes a close slip fit within the tip. The forward end of drive wire 96 is rigidly secured to an inner sidewall of the injection piston, leaving an open passage 120 through the piston The forward end of the piston is flat to make a mating fit with the rear surface of an electrode assembly (not shown) so the electrode assembly is held in place against the piston when chamber 93 (and hence the interior of tube 85 and passage 120) is evacuated. A longitudinal slot 122 is formed in the outer end of the sidewall of tip 86, and provides clearance space for lead wires extending from the electrode assembly, as well as venting of the evacuated interior of the tool after the electrode is inserted.

In use, tube 94 is connected to a vacuum pump, and tool 80 is cocked by retracting knob 102 until tip 91 of trigger 90 is urged downwardly by a trigger spring (not shown) into engagement with recess 92 in piston 88. In this cocked position as shown in FIG. 6, injection piston 119 is retracted within curved tip 86, and the vacuum pump reduces the pressure within chamber 93 and tube 85 to about 300 to 400 millimeters of mercury below ambient air pressure. The electrode assembly is sucked into the curved tip to seat the assembly base against the front of the injection piston, with lead wires of the electrode assembly fitted through slot 122.

The surgeon then places the end of the tool tip against the surface of the cochlear nucleus, and fires the tool by depressing trigger 90. Electrode insertion speed is controlled and adjustable by the extent of compression of spring 99, the level of vacuum formed within the tool, and the setting of screw 110 which adjusts the degree of viscous damping of forward velocity. A preferred range of insertion speed is 0.5 to 2 meters per second.

When the tool is fired, piston 88 moves forwardly to occlude tube 94, and thereby to disconnect the vacuum source from the tool interior. Simultaneously, the rear end of the injection piston moves forwardly to an extended position which is ahead of the rear end of slot 122, thus venting the interior of the curved tip to ambient pressure, and releasing the now-inserted electrode assembly. Release of the electrode assembly occurs within a few milliseconds so inadvertent post-firing movement of the tool does not affect the inserted electrode assembly.

Tool 80 can of course also be used with a straight tube 16 as shown in FIGS. 1 and 3, and is illustrated with a curved tube to show the suitability of the tool for electrode insertion in the cochlear nucleus.

Figure 9:
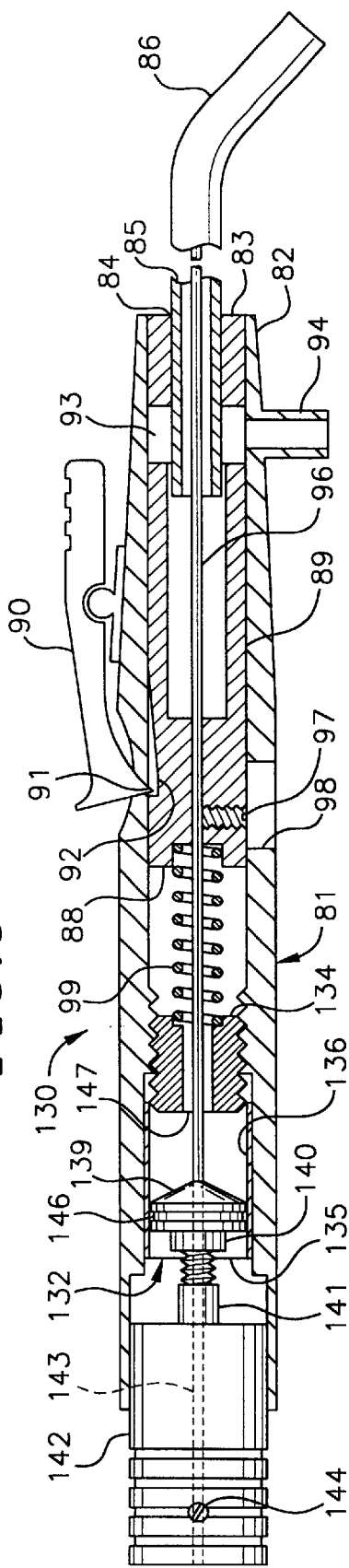
FIG. 9 is a sectional side elevation of a third embodiment similar to FIG. 6, but using a different style of velocity-controlling damping mechanism.
Figure 11:
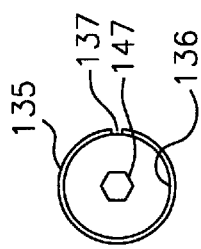
FIG. 11 is an end view on line 11—11 of FIG. 10.
Figure 10:
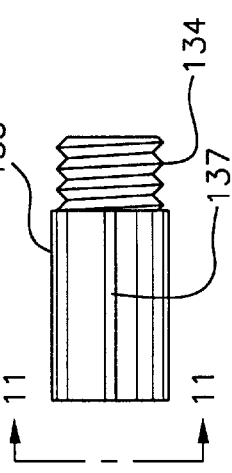
FIG. 10 is a side elevation of several components of the damping mechanism.

FIGS. 9–11 illustrate a third and presently preferred embodiment of an insertion tool 130 of this invention. The components of tool 130 extending from compression coil spring 99 to tip 86 are identical to those shown in FIGS. 6 and 8 with respect to tool 80, and those parts are not renumbered, and need not be reidentified. The difference between tools 80 and 130 resides in the substitution of a viscous-friction damping assembly 132 which is free of silicone grease, and is hence more readily sterilized.

Assembly 132 includes a spring compression plug 134 (corresponding in shape and function to plug 100 in tool 80) to the rear end of which is cemented or otherwise secured a thin-wall plastic tube or cylinder 135 having a bore 136. The cylinder typically has an outside diameter of about 0.40 inch, and an inside diameter of about 0.34 inch, and can be made of polyethylene. The cylinder makes a loose slip fit within central bore 89 of housing 81. A single narrow slit 137 is cut in the sidewall of cylinder 135 as shown in FIGS. 10 and 11.

A resilient piston 139 made of an elastomer such as Neoprene is cemented at its rear end to the head of a plastic screw 140 corresponding to screw 110 of tool 80. The screw is threaded into a mating threaded bore centrally formed in a stud or sleeve 141 integrally formed with and extending from a cylindrical cocking knob 142 (corresponding to knob 102 of tool 80). A central bore 143 extends through the piston, screw, sleeve and cocking knob to receive drive wire 96 which is secured to the knob by a set screw 144.

Piston 139 has a circumferential groove 146, and the piston makes a snug slip fit within cylinder 135 to slightly expand slit 137. It has been found that the compressive force of the slit cylinder against the accelerating piston when the tool is actuated or fired approximates the desired viscous damping which permits high initial acceleration followed by stabilization of velocity.

Just as in tool 80, spring compression plug 134 has a central hexagonal bore 147 to enable adjustment of longitudinal position of the plug which in turn establishes the compression of spring 99 when the tool is cocked. Access to the bore is achieved by loosening set screw 144 and withdrawing the cocking knob and piston. A hollow hexagonal key (not shown) can then be fitted over drive wire 96 and fitted into bore 146 to rotate the plug.

There have been described several embodiments of an electrode insertion tool which can be handheld for precision placement of an electrode assembly which is then inserted into tissue with good penetration and minimum risk of tissue damage. Depending on the nature of the tissue to be penetrated, insertion speeds in the range of one-to-four meters per second are typical, and are selected by the degree of compression of the cocked actuating spring.

What is claimed is:

1. An electrode insertion tool, comprising:
   a hollow handle having a rear end, and a front end which terminates in a reduced-diameter tubular extension in which is moveably positioned an injector, an electrode assembly to be inserted being fully receivable within the tubular extension adjacent the injector;
   spring means positioned within the handle between an adjustable and normally fixed plug and a moveable ring, and a trigger for holding the ring when the spring is compressed and actuable to release the ring;

a cocking knob extending from and moveable within the rear end of the handle;

an elongated connecting means extending within the handle and secured to the injector, moveable ring and cocking knob, whereby retraction of the knob retracts the injector and ring to compress the spring means;

a damping means within the handle, and having a stationary part secured to the connecting means for applying a force approximating viscous damping to the connecting means, whereby release of the ring by actuation of the trigger causes high initial acceleration of the connecting means to drive the electrode out of the tubular extension for initial penetration of a tissue surface, followed by controlled velocity of the connecting means and electrode.

2. The tool of claim 1 in which the spring means is a compression coil spring, and the connecting means is a rigid rod.

3. The tool of claim 1 in which the damping means includes a magnet for generating an eddy-current braking force.

4. The tool of claim 1 in which the damping means includes a cylinder positioned within the housing, and a piston moveably fitted within the cylinder and secured to the connecting means.

5. The tool of claim 4 in which the cylinder has a sidewall with a narrow longitudinal slit which is expanded by insertion of the piston.

6. The tool of claim 1, and further comprising means for coupling a vacuum source to the tubular extension to hold an electrode assembly against the injector until the tool is accuated to eject the electrode assembly.

* * * * *